United States Patent
Li et al.

(10) Patent No.: US 7,883,334 B2
(45) Date of Patent: Feb. 8, 2011

(54) METHOD AND SYSTEM FOR PROVIDING ALTERNATING USE ORTHODONTIC ALIGNERS

(75) Inventors: Chunhua Li, Cupertino, CA (US); Eric Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 231 days.

(21) Appl. No.: 11/757,299

(22) Filed: Jun. 1, 2007

(65) Prior Publication Data

US 2008/0299507 A1    Dec. 4, 2008

(51) Int. Cl.
*A61C 3/00*    (2006.01)
(52) U.S. Cl. ............................................. 433/24; 433/6
(58) Field of Classification Search ...................... 433/6, 433/24; D24/180; 128/861
See application file for complete search history.

(56) References Cited

U.S. PATENT DOCUMENTS

| | | | | |
|---|---|---|---|---|
| 4,139,944 A * | 2/1979 | Bergersen | ...................... | 433/6 |
| 6,488,499 B1 * | 12/2002 | Miller | .......................... | 433/24 |
| 6,607,382 B1 * | 8/2003 | Kuo et al. | ....................... | 433/6 |
| 2002/0142258 A1 * | 10/2002 | Chishti et al. | ................... | 433/6 |
| 2003/0207224 A1 * | 11/2003 | Lotte | .............................. | 433/6 |
| 2005/0100853 A1 * | 5/2005 | Tadros et al. | .................... | 433/6 |
| 2006/0008760 A1 * | 1/2006 | Phan et al. | ...................... | 433/6 |
| 2006/0078841 A1 * | 4/2006 | DeSimone et al. | ............. | 433/6 |

* cited by examiner

*Primary Examiner*—Cris L Rodriguez
*Assistant Examiner*—Eric Rosen
(74) *Attorney, Agent, or Firm*—Beyer Law Group LLP

(57) ABSTRACT

Method and system for providing a first appliance configured for positioning substantially around one or more teeth during a first portion of a recurring time period to apply one of a first predetermined force or a predetermined tooth movement on the one or more teeth, the first appliance formed of a first material, a second appliance configured for positioning substantially around the one or more teeth during a second portion of the recurring time period to apply one of a second predetermined force or a predetermined tooth movement on the one or more teeth, the second appliance formed of a second material, where at least one of the first portion and the second portion of the recurring time period is repeated at least once such that at least one of the first appliance or the second appliance is positioned again substantially around the one or more teeth during the respective first or second portion of the recurring time period are provided.

40 Claims, 3 Drawing Sheets

METHOD AND SYSTEM FOR PROVIDING ALTERNATING USE ORTHODONTIC ALIGNERS

FIELD OF THE INVENTION

The present invention is related generally to the field of orthodontics. More specifically, the present invention is related to methods and system for providing use specific orthodontic aligners.

BACKGROUND

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing "braces" as commonly referred to. Typical braces include a variety of appliances such as brackets, bands, archwires, ligatures, and O-rings. After braces are bonded to the teeth, periodic meetings with an orthodontist are typically required to reactively adjust the braces. This may involve installing and/or adjusting different archwires with different force-inducing properties and/or may include replacing or tightening wire-to-bracket ligatures. Between visits with the orthodontist, the patient may be required to wear supplementary appliances, such as elastic bands or headgear, to supply additional or supplemental extraoral forces.

In view of the foregoing, it would be desirable to have methods for providing orthodontic aligners that may be customized for use during different time periods for example, within each treatment stage by providing additional choice to the patient to customize the orthodontic treatment plan and progress.

SUMMARY OF THE INVENTION

In view of the foregoing, one aspect of the present invention for providing orthodontic treatment includes a system and method where a first appliance configured for positioning substantially around one or more teeth during a first portion of a recurring time period to apply a first predetermined force or predetermined tooth movement on the one or more teeth, the first appliance formed of a first material, a second appliance configured for positioning substantially around the one or more teeth during a second portion of the recurring time period to apply a second predetermined force or predetermined tooth movement on the one or more teeth, the second appliance formed of a second material, where at least one of the first portion and the second portion of the recurring time period is repeated at least once such that at least one of the first appliance or the second appliance is positioned again substantially around the one or more teeth during the respective first or second portion of the recurring time period.

These and other features and advantages of the present invention will be understood upon consideration of the following detailed description of the invention and the accompanying drawings.

DETAILED DESCRIPTION

Figure 1:
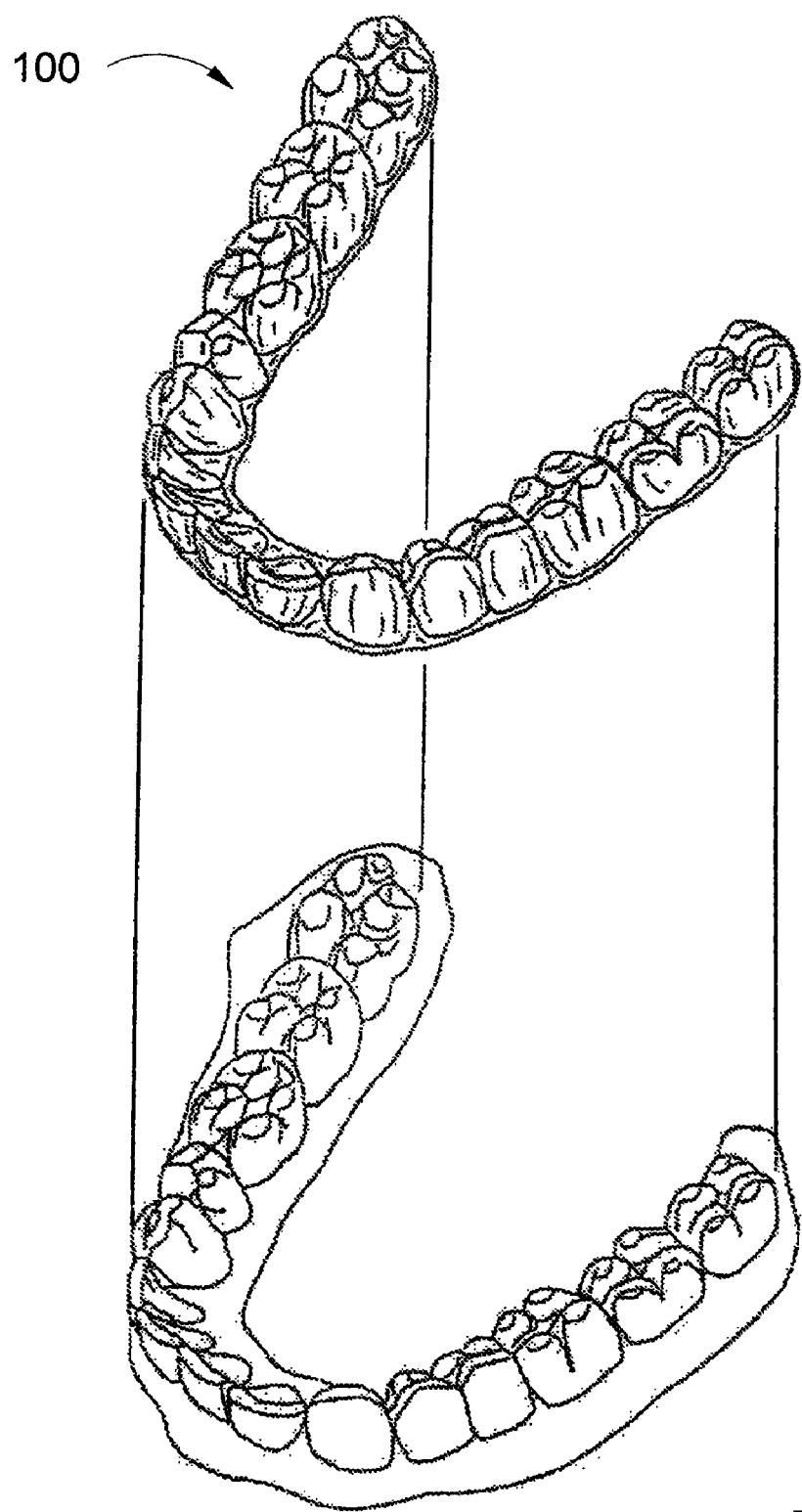
FIG. 1 is a perspective view of a removable dental positioning appliance that may be formed by one or more of the materials and methods in accordance with the embodiments of the present invention.

Referring to FIG. 1, systems and method in accordance with the various embodiments of the present invention include a plurality of incremental position adjustment appliances, each comprised of different material, for each treatment stage of orthodontic treatment. As described in further detail below, the orthodontic appliances may be configured to incrementally reposition individual teeth in the jaw. In one aspect, a pair of orthodontic appliances are provided for wear by a patient sequentially and alternatingly during each stage of the orthodontic treatment to achieve the gradual tooth repositioning.

In one aspect, an appliance 100 as shown in FIG. 1 may be provided which comprise a polymeric shell having a cavity shaped to receive and resiliently reposition teeth from one tooth arrangement to a successive tooth arrangement. The polymeric shell may be configured to fit over all or fewer than all the teeth present in the upper or lower jaw. Often, only certain one(s) of the teeth will be repositioned while others of the teeth will be designated as a base or anchor region for holding the repositioning appliance in place as it applies the resilient repositioning force against the tooth or teeth intended to be repositioned.

In complex cases, however, many or most of the teeth may be repositioned at some point during the treatment. In such cases, the teeth which are moved can also serve as a base or anchor region for holding the repositioning appliance. Additionally, the gums and/or the palate can serve as an anchor region, thus allowing all or nearly all of the teeth to be repositioned simultaneously.

In one aspect, the orthodontic appliance may include a thin shell of elastic material that generally conforms to a patient's teeth, but that is slightly out of alignment with the patient's initial tooth configuration. Placement of the elastic positioner over the teeth applies controlled forces in specific locations to gradually move the teeth into the new configuration. Repetition of this process with successive appliances having different configurations eventually moves a patient's teeth through a series of intermediate configurations to a final desired configuration. Additional detailed description of exemplary elastic polymeric positioning appliances and methods of using the same are described in U.S. Pat. No. 6,217,325 commonly assigned to the assignee of the present invention, and the disclosure of which is incorporated by reference for all purposes.

In one embodiment of the present invention, one of the pair or plurality of appliances provided for each stage of the orthodontic treatment may include a polymeric appliance 100 such as shown in FIG. 1 formed from a thin sheet of a suitable elastomeric polymeric, such as Tru-Tain 0.03 in. thermal forming dental material, Tru-Tain Plastics, Rochester, Minn. 55902. Moreover, an additional appliance having substantially the same shape or mold is also provided and which may be formed of a different material which provide for a different stiffness or resilience. In this manner, in one embodiment, a patient or a user may alternately use one of the pair of orthodontic appliances during each treatment stage depending upon the patient's preferred usage time or desired treatment time period for each treatment stage.

No wires or other means may be provided for holding the appliance 100 in place over the teeth. In some cases, however, it may be desirable or necessary to provide individual anchors on teeth with corresponding receptacles or apertures in the appliance 100 so that the appliance 100 can apply a retentive or other directional orthodontic force on the tooth which would not be possible in the absence of such an anchor.

In this manner, in one embodiment of the present invention, the patient or the user may be provided with a pair of substantially identical appliances (that is, where the cavity geometry of the two appliances are substantially the same) for each treatment stage, where each of the pair of the substantially identical appliances may be formed of different material. For example, one appliance may comprise a clear or substantially transparent appliance that is aesthetically more appealing, and further, the other appliance may comprise an opaque material such as, for example, but not limited to, semi-crystalline thermoplastic, or co-polymers thereof, with or without any filler or reinforcement material provided therein.

More specifically, using a pair of appliances that have different material composition and thus providing different stiffness or resilience, the patient or the user may customize the use of each of the pair of appliances in an alternating manner depending upon various factors or circumstances, such as, but not limited to, day time use and night time use, during function or non-function (chewing vs. non-chewing), during social settings (where appearance may be more important) and nonsocial settings (where the aesthetic appearance may not be a significant factor), or based on the patient's desire to accelerate the teeth movement (by optionally using the more stiff appliance for a longer period of time as opposed to the less stiff appliance for each treatment stage).

For example, in one aspect, the patient or the user may be provided with a clear orthodontic appliance that may be primarily used to retain the position of the teeth, and an opaque orthodontic appliance that may be primarily used to move the teeth for each treatment stage. Accordingly, during the day time, in social settings, or otherwise in an environment where the patient is more acutely aware of the physical appearance, the patient may use the clear appliance. Moreover, during the evening or night time, in non-social settings, or otherwise when in an environment where physical appearance is less important, the patient may use the opaque appliance that is configured to apply a different amount of force or otherwise has a stiffer configuration to accelerate the teeth movement during each treatment stage. This approach may be repeated so that each of the pair of appliances are alternately used during each treatment stage.

If the intrinsic natural color of the teeth is undesirable, it may also be possible that the tooth movement be accomplished by a masking opaque color in the aligner material, and the teeth retained by an alternate material which may be clear or of a different opacity than the treating color.

In this manner, in one aspect of the present invention, the patient or the user is provided with a certain level of control over the orthodontic treatment progress, by alternating the use between the pair of appliances manufactured with different materials. In a further aspect, the doctor may associate each treatment stage based on a predetermined number of hours of usage of one or more of the pair of appliances provided to the patient. For example, given that the opaque or colored appliance may be configured to provide relatively faster teeth movement (as compared to the clear appliance) for each treatment stage, the doctor may establish the orthodontic treatment plan based on the patient's usage of the opaque appliance for a predetermined number of hours, before the patient or the user may move on to the next treatment stage.

In an additional embodiment, the patient may prefer to use the opaque or colored appliance for aesthetic purposes, and in which case, the patient or the user may optionally and primarily use the opaque or colored appliance for each treatment stage. Further, the appliance suited for the upper teeth and the lower teeth may each be provided with a pair of clear appliance and opaque appliance such that the patient or the user may customize the usage of the two different appliances—for example, using a clear appliance for the upper teeth, while simultaneously using the opaque appliance for the lower teeth, for each treatment stage.

In still another aspect, the opaque appliance may be provided with additional features such as patterns, marks, or any other type of customized aesthetic appearance that may be desirable to the patient or the user. Additionally, based on the composition of the material used to form each of the pair of appliances for each treatment stage, in one embodiment, the clear or transparent appliance may be configured to retain the teeth in position, while the opaque or colored appliance may be configured to reposition the teeth. Accordingly, by alternating the use between the clear or transparent appliance and the opaque or colored appliance during each treatment stage, in one aspect, the orthodontic treatment may be more effective in repositioning the teeth, for example, by minimizing or lessening the effects of material stress relaxation and creep which the appliances may undergo during usage and that may degrade the ability to reposition the teeth as desired and/or within the desired time frame.

In one aspect of the present invention, the clear or substantially transparent appliance may be made of transparent polymeric material that may include, for example, but not limited to one or more of amorphous thermoplastic polymers, semi-crystalline thermoplastic polymers and transparent thermoplastic polymers with low amount fillers or nanofillers, such as one or more of polycarbonate, thermoplastic polyurethane, acrylic, polysulfone, polyprolylene, polypropylene/ethylene copolymer, or polyester/polycarbonate copolymer, styrenic polymeric materials, polyamide, polymethylpentene and polyetheretherketone.

Additionally, in one embodiment, the opaque or colored appliance may comprise one or more of semi-crystalline thermoplastic, crystalline thermoplastics and composite, such as polyamide, polyethylene terephthalate. polybutylene terephthalate, polyetherimide, polyetheretherketone, polyethersulfone, or polytrimethylene terephthalate, and composites with fillers or nanofillers.

Moreover, in still a further aspect, the filler or nanofiller of each of the clear or transparent appliance and the opaque or colored appliance may include one or more filler or reinforcing material that includes, for example, but not limited to or more of carbon (including carbon fibers), mineral, silica, titanium, metal oxide, oxygenates, halides and sulfates, short or long glass fibers, synthetic alumina nanofillers, aluminorganic nanofillers, calcium carbonate nanofillers, ceramic nanofillers, carbon black nanofillers, carbon nanotube nanofillers, carbon fiber nanofillers, cellulose nanofillers, activated clay nanofillers, natural clay nanofillers (mined, refined, and treated), synthetic clay nanofillers, organo clay nanofillers, natural fiber nanofillers, graphite nanofillers, magnesium hydroxide nanofillers, mineral nanofillers, montmorillonite clay nanofillers, phosphate nanofillers, poly oligomeric silsesquioxane (POSS) nanofillers, silica nanofillers, silver nanofillers, talc nanofillers, organo-titanate nanofillers, titanium white nanofillers and zinc oxide nanofillers.

The material may also be impregnated with metal ions and metal ion complexes including gold, silver, copper, and/or fluoride, to impart antimicrobial benefit.

In this manner, in one aspect of the present invention, there are provided methods and systems for repositioning teeth from an initial tooth arrangement to a final tooth arrangement using alternating orthodontic appliances. Repositioning teeth is accomplished by a series of alternating appliances configured to receive the teeth in a cavity and incrementally reposition individual teeth in a series of at least three successive steps, usually including at least four successive steps, often including at least ten steps, sometimes including at least twenty-five steps, and occasionally including forty or more steps, and where each step requires the use of two alternating appliances that are formed of different materials, that exhibit differing properties including, for example, stiffness, resilience, and the like.

In a further aspect, the varied stiffness or resiliency of the one (or more) of the two (or more) alternating appliances may be provided using, for example, in combination with the material composition described above (or without the material composition described above), components such as wires embedded in the orthodontic appliance, layered or laminated material provided on the orthodontic appliance, or any other suitable approaches to modify or otherwise vary the elastic moduluses along different and/or additional axes relative to the position of the teeth in relation to the orthodontic appliance. Additional examples including detailed descriptions are provided in U.S. Pat. No. 6,572,372 titled "Embedded Features and Methods of a Dental Appliance" issued Jun. 3, 2003, and commonly assigned to the assignee of the present application, in U.S. Pat. No. 6,524,101 titled "System and Methods for Varying Elastic Modulus Appliances, issued Feb. 25, 2003, commonly assigned to the assignee of the present application, and in U.S. Pat. No. 6,454,565 titled "System and Methods for Varying Elastic Modulus Appliances" issued Sep. 24, 2002, commonly assigned to assignee of the present application, the disclosures of each of which are herein incorporated by reference for all purposes.

Referring again to FIG. 1, each pair of appliances in one embodiment may comprise polymeric shells (formed with different materials) having the teeth-receiving cavity (that may be substantially the same or slightly different) formed therein. Each pair of appliances may be configured so that its tooth-receiving cavity has a geometry corresponding to an intermediate or end tooth arrangement intended for that pair of appliances. That is, when a pair of appliances are alternatingly worn by the patient or the user, certain of the teeth will be misaligned relative to an undeformed geometry of the respective appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

In one aspect, the system according to the present invention may include at least a first pair of appliances (transparent and opaque) to be alternately used and having a geometry selected to reposition a patient's teeth from the initial tooth arrangement to a first intermediate arrangement where individual teeth will be incrementally repositioned. The system may further comprise at least one intermediate pair of appliances having a geometry selective to progressively reposition teeth from the first intermediate arrangement to one or more successive intermediate arrangements. The system may still further comprise a final pair of appliances having a geometry selected to progressively reposition teeth from the last intermediate arrangement to the desired final tooth arrangement. In some cases, it may be desirable to form the final pair of appliances or several pairs of appliances to "over correct" the final tooth position.

The final pair of appliances or several pairs of appliances in the series may have a geometry or geometries selected to over correct the tooth arrangement, i.e. have a geometry which would (if fully achieved) move individual teeth beyond the tooth arrangement which has been selected as the "final." Such over correction may be desirable in order to offset potential relapse after the repositioning method has been terminated, i.e. to permit some movement of individual teeth back toward their pre-corrected positions. Over correction may also be beneficial to speed the rate of correction, i.e. by having a pair of appliances with a geometry that is positioned beyond a desired intermediate or final position, the individual teeth will be shifted toward the position at a greater rate. In such cases, treatment may be terminated before the teeth reach the positions defined by the final pair of appliances or pairs of appliances. Successive pairs of appliances may be replaced when the teeth either approach (within a preselected tolerance) or have reached the target end arrangement for that stage of treatment, typically being replaced at an interval in the range from 2 days to 20 days, usually at an interval in the range from 5 days to 10 days.

For example, the transition to the next pair of appliances may be based on a number of factors. Most simply, the appliances can be replaced on a predetermined schedule or at a fixed time interval (i.e. number of days for each pair of appliances or number of hours associated with the opaque appliance at each treatment stage) determined at the outset (for example, before manufacturing, at the time of treatment diagnosis and planning, in between treatment stages, or post manufacturing and prior to start of each stage) based on an expected, typical or actual patient response. Indeed, actual patient response can be taken into account, e.g. a patient can advance to the next pair of appliances when that patient no longer perceives pressure on their teeth from a current pair of appliances, i.e. the pair of appliances they have been wearing fits easily over the patient's teeth and the patient experiences little or no pressure or discomfort on his or her teeth.

In some cases, for patients whose teeth are responding very quickly, it may be possible for a treating professional to decide to skip one or more intermediate pairs of appliances, i.e. reduce the total number of appliances being used below the number determined at the outset. In this way, the overall treatment time for a particular patient can be reduced. In one aspect, the tooth positions defined by the cavities in each successive geometry may differ from those defined by the prior geometry by no more than 2 mm, preferably no more than 1 mm, and often no more than 0.5 mm.

Figure 2:
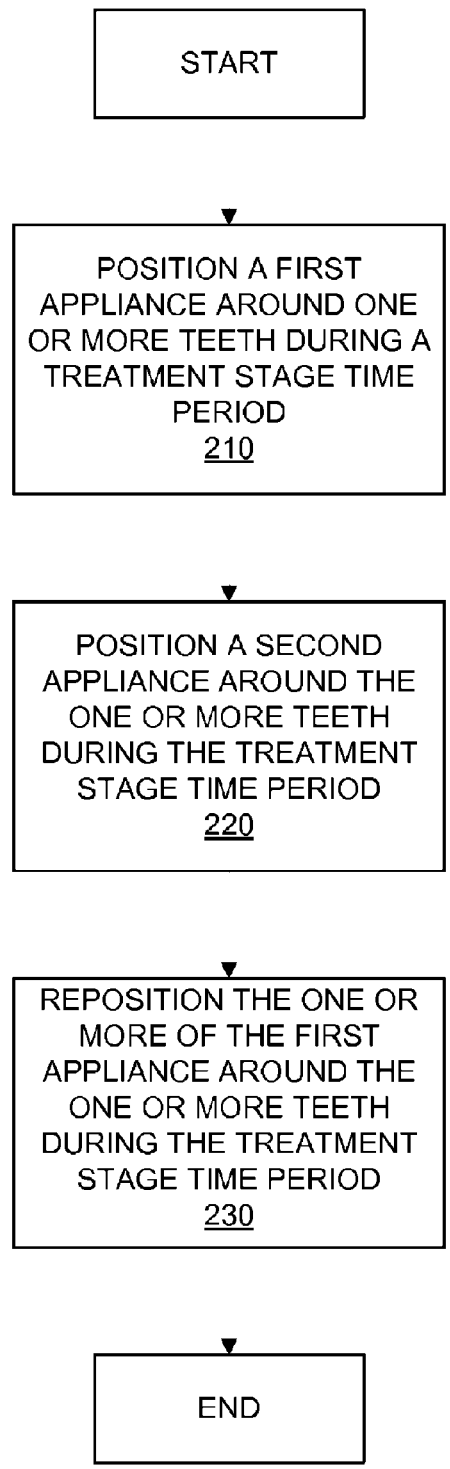
FIG. 2 is a flowchart illustrating an alternating use of orthodontic aligners in accordance with one embodiment of the present invention.

FIG. 2 is a flowchart illustrating an alternating use of orthodontic aligners in accordance with one embodiment of the present invention. Referring to FIG. 2, at step 210, a first appliance (for example, the clear or substantially transparent appliance) is positioned around one or more teeth during a treatment stage time period. In one aspect, the treatment stage time period may include, for example, but not limited to, a first portion and a second portion of a recurring time period, where the recurring time period may include one or more of a sleeping time period and a nonsleeping time period, respectively, a weekday time period and a weekend time period, respectively, an outdoor time period and an indoor time period, respectively, a jaw functioning and a non-functioning time period, respectively, or a social time period and a non social time period, respectively.

Further, in an additional aspect, the treatment stage time period including the first portion and the second portion of the recurring time period may correspond to a relatively faster movement of the one or more teeth, and a relatively slower movement of the one or more teeth, respectively, or a relatively greater amount of force applied to one or more teeth, and a relatively less amount of force applied to the one or more teeth, respectively. While specific examples of time periods for the treatment stage time period is provided herein, the present disclosure is not limited to the examples described above, and other suitable treatment stage time periods may be contemplated.

Thereafter, the first appliance is removed during the same treatment stage time period, and at step 220, a second appliance (for example, the opaque or colored appliance) is positioned around the one or more teeth again, during the same treatment stage time period. After a predetermined period of time of using the second appliance, the first appliance is again repositioned over the one or more teeth at step 230.

In this manner, in one aspect of the present invention, a plurality of orthodontic appliances may be provided, where each appliance is used or worn by the user or the patient for a predetermined time period (or during a desired time period as determined by the patient or the user), and further, where each appliance is alternately worn or used during each treatment stage of an orthodontic treatment plan. While the use of two appliances is described herein, within the scope of the invention, additional appliances (each having a different material composition, and therefore, differing stiffness or resilience) may be provided for each treatment stage, and during which, the patient or the user may rotate the usage of each of the plurality or additional appliances.

Figure 3:
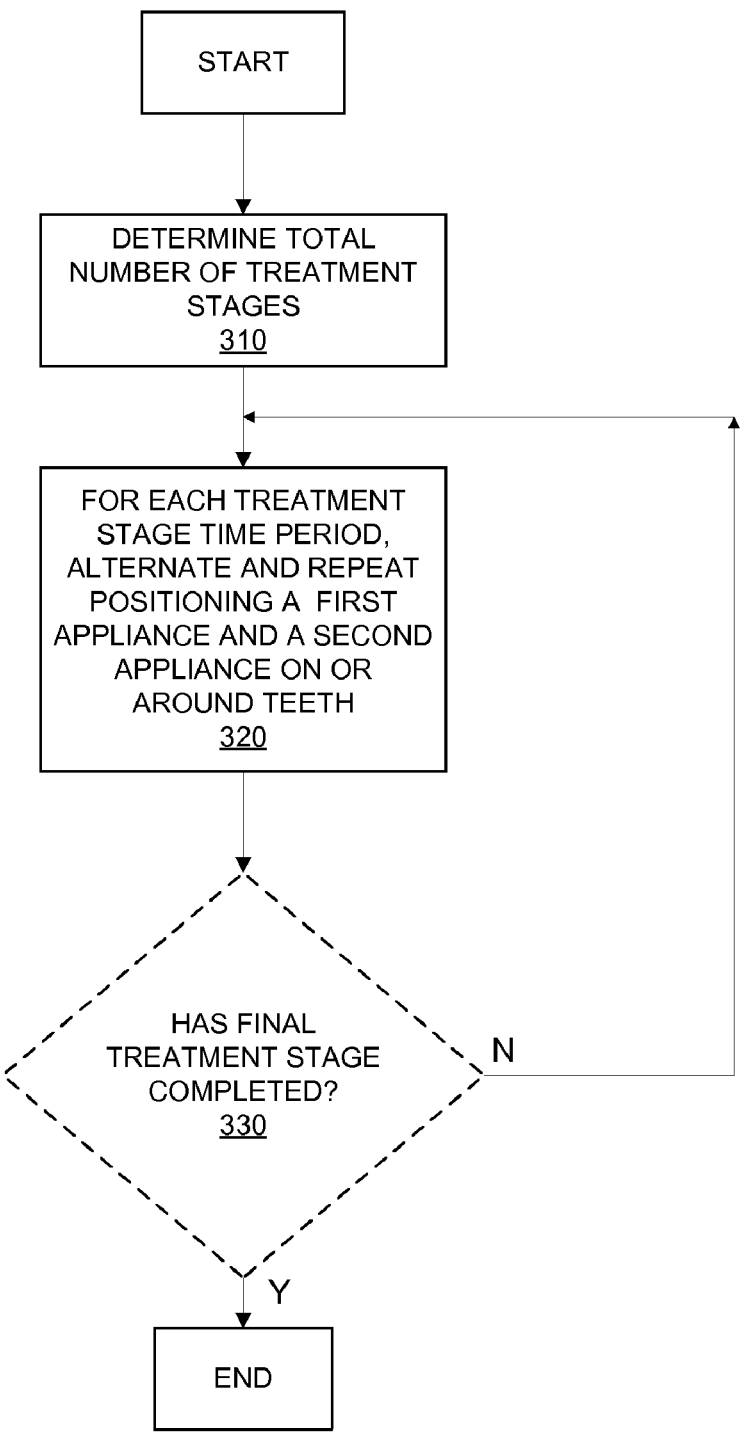
FIG. 3 is a flowchart illustrating an alternating use of orthodontic aligners in accordance with another embodiment of the present invention.

FIG. 3 is a flowchart illustrating an alternating use of orthodontic aligners in accordance with another embodiment of the present invention. Referring to FIG. 3, initially the total number of treatment stages is determined at step 310. That is, the total number of treatment stages for the treatment of the patient's orthodontic condition based on the alternating use orthodontic aligners is determined. It is to be noted that each treatment stage in one embodiment includes a different pair of orthodontic aligners, and further, each of the orthodontic aligner in each treatment stage in one embodiment includes one or more different configuration, geometry, or composition.

Thereafter, at step 320, for each treatment stage determined, first and second appliances are alternatingly and repeatedly positioned on or around the one or more teeth, where each of the first and second appliances comprise a different material composition. If at step 330 it is determined that the final treatment stage has not been completed, then the first and second appliances are again alternatingly and repeatedly positioned on or around the one or more teeth until the final treatment stage is completed.

In this manner, in one aspect, there is provided an orthodontic treatment that includes a system and method of alternately using a plurality of orthodontic appliances each having one or more different geometry, configuration, composition, or property, and where during each treatment stage time period, the plurality of orthodontic appliances are alternatingly and repeatedly positioned over the patient's until the completion of the treatment stage time period so as to progress to the subsequent treatment time period.

In a further aspect, the alternating use orthodontic appliances may include an intra-oral therapeutic agent delivery mechanism to allow the delivery of drug or therapeutic agent through the mouth. For example, in one aspect, the orthodontic appliance described above may be configured to contain and release the drug or therapeutic agent to the oral environment at a predetermined delivery or release rate when the orthodontic appliance is positioned over the teeth. More specifically, the orthodontic appliance described above may include a layer that includes the therapeutic agent, where the layer may be formed over at least a portion of the surfaces of the orthodontic appliance.

Moreover, the layer may include the therapeutic agent in or on a carrier or binder which promotes adhesion or attachment to the orthodontic appliance and/or which creates a matrix from which the therapeutic agent may be released by diffusion or dissolution. Further, the therapeutic agent or drug may be encapsulated or suspended in the layer, or still in accordance with another aspect, the orthodontic appliance may itself comprise a controlled-release material containing the therapeutic agent or drug.

Additionally, within the scope of the present disclosure, the therapeutic agent or drug may be provided in or on one or more of the alternating use orthodontic appliances for each treatment stage time period. Additional embodiments and further detailed disclosure related to intra-oral therapeutic agent or drug delivery is provided in pending U.S. patent application Ser. No. 11/000,282 filed on Nov. 30, 2004, commonly assigned to the assignee of the present application, the disclosure of which is incorporated in its entirely by reference for all purposes.

Accordingly, in one aspect, a system for providing orthodontic treatment includes a first appliance configured for positioning substantially around one or more teeth during a first portion of a recurring time period to apply a first predetermined force or predetermined tooth movement on the one or more teeth, the first appliance formed of a first material, and a second appliance configured for positioning substantially around the one or more teeth during a second portion of the recurring time period to apply a second predetermined force or predetermined tooth movement on the one or more teeth, the second appliance formed of a second material, where at least one of the first portion and the second portion of the recurring time period is repeated at least once such that at least one of the first appliance or the second appliance is positioned again substantially around the one or more teeth during the respective first or second portion of the recurring time period.

The recurring time period may be repeated, and further, where the first portion and the second portion of each repeated recurring time period may be nonoverlapping.

In one aspect, the first material may have clarity of approximately 80 percent or more, and where the first material may include one or more of amorphous thermoplastic polymer, semi-crystalline thermoplastic polymer, transparent thermoplastic polymer with one or more filler, reinforcement, or nanofiller material, polycarbonate, thermoplastic polyurethane, acrylic, polysulfone, polyprolylene, polypropylene/ethylene copolymer, or polyester/polycarbonate copolymer, styrenic polymeric material, polyamide, polymethylpentene and polyetheretherketone.

Further, in another aspect, the second material may have clarity of less than approximately 80 percent, and further, where the second material may include semi-crystal thermoplastic, crystalline thermoplastic, polyamide, polyethylene terephthalate. polybutylene terephthalate, polyetherimide, polyetheretherketone, polyethersulfone, or polytrimethylene terephthalate, or one or more composites with one or more filler or nanofiller.

In still another aspect, the one or more of the first material and the second material may included one or more filler, reinforcement material or nanofiller material, where the one or more filler, reinforcement material or the nanofiller material may include one or more of carbon (including carbon fiber), mineral, silica or titanium, metal oxide, oxygenate, halide, sulfate, short or long glass fiber, synthetic alumina nanofiller, aluminorganic nanofiller, calcium carbonate nanofiller, ceramic nanofiller, carbon black nanofiller, carbon nanotube nanofiller, carbon fiber nanofiller, cellulose nanofiller, activated clay nanofiller, natural clay nanofiller (mined, refined and treated), synthetic clay nanofiller, organo clay nanofiller, natural fiber nanofiller, graphite nanofiller, magnesium hydroxide nanofiller, mineral nanofiller, montmorillonite clay nanofiller, phosphate nanofiller, poly oligomeric silsesquioxane (POSS) nanofiller, silica nanofiller, silver nanofiller, talc nanofiller, organo-titanate nanofiller, titanium white nanofiller, or zinc oxide nanofiller.

In still another aspect, the second material may include a copolymer, a blend of polymers, or a composite material, and further, where the one or more copolymer or the composite material may include one or more of polycarbonate/glass fiber, polycarbonate/acrylic alloy, polycarbonate/ABS alloy, polysulfone/polycarbonate alloy, or polycarbonate/copolyester, liquid crystal polymer or glass reinforced liquid crystal polymer.

In one aspect, the first predetermined force or predetermined tooth movement (or the associated force retention) may be less than the second predetermined force or predetermined tooth movement (or the respective associated force retention).

In another aspect, the first predetermined force or predetermined tooth movement (or the associated force retention) may be substantially equal to the second predetermined force or predetermined tooth movement (or the respective associated force retention).

In still another aspect, the one of the first appliance and the second appliance may have a relatively higher opacity than the other one of the first appliance and the second appliance.

Further, the one of the first appliance and the second appliance may be configured primarily to retain the position of the one or more teeth, and further, where the other one of the first appliance and the second appliance may be configured to primarily displace the position of the one or more teeth.

In still another aspect, the one of the first appliance and the second appliance may be substantially translucent, and further, where the other one of the first appliance and the second appliance may be substantially opaque.

Also, each of the first appliance and the second appliance may include one or more cavities formed substantially to surround a respective one or more of the teeth, and further, where the cavity geometry of the first appliance and the second appliance may be substantially the same.

Additionally, each of the first appliance and second appliance may include a plurality of dental aligners, a first of the plurality of dental aligners including an upper teeth dental aligner and a lower teeth dental aligner, and where the one or more of the upper teeth dental aligner or the lower teeth aligner may be formed of one of a clear material or a colored material.

The first portion and the second portion of the recurring time period may include one or more of a sleeping time period and a nonsleeping time period, respectively, a weekday time period and a weekend time period, respectively, an outdoor time period and an indoor time period, respectively, or a social time period and a non social time period, respectively.

The first portion and the second portion of the recurring time period each may correspond to one of a relatively faster movement of the one or more teeth or a relatively slower movement of the one or more teeth.

Moreover, after a predetermined number of recurring time periods the first appliance and the second appliance may be modified to apply a modified first predetermined force or predetermined tooth movement and a modified second predetermined force or predetermined tooth movement on the one or more teeth, where the first appliance and the second appliance each may include one or more cavities for substantially surrounding the one or more teeth such that, the one or more cavities are modified after the predetermined number of recurring time periods.

A system of providing orthodontic treatment in accordance with another embodiment of the present invention includes a plurality of orthodontic treatment stages, each treatment stage including, a first appliance configured for positioning substantially around one or more teeth during a first portion of a recurring time period to apply a first predetermined force or predetermined tooth movement on the one or more teeth, the first appliance formed of a first material, a second appliance configured for positioning substantially around the one or more teeth during a second portion of the recurring time period to apply a second predetermined force or predetermined tooth movement on the one or more teeth, the second appliance formed of a second material, where at least one of the first portion and the second portion of the recurring time period is repeated at least once such that at least one of the first appliance or the second appliance is positioned again substantially around the one or more teeth during the respective first or second portion of the recurring time period, and where for each treatment stage, the number of recurring time period is determined based on a predetermined treatment parameter.

The predetermined treatment parameter may include one of a treatment prescription, or a predetermined number of hours of usage of the one or more of the first appliance or the second appliance.

A dental appliance configured for moving teeth in accordance with still another embodiment may include a polymeric shell configured for positioning over one or more teeth, the polymeric shell formed of one or more of a semi-crystalline thermoplastic, a co-polymer of a semi-crystalline thermoplastic, a composite material, or a filler material, where the polymeric shell is configured to resiliently reposition the one or more teeth from a first predetermined position to a second predetermined position, and further, where the polymeric shell is positioned over the one or more teeth during a portion of a plurality of recurring time periods.

The semi-crystalline thermoplastic may include polyamide, polyethylene terephthalate. polybutylene terephthalate, polyetherimide, polyetheretherketone, polyethersulfone, or polytrimethylene terephthalate.

The one or more filler material may include one or more of carbon, mineral, silica or titanium.

The one or more co-polymer or the composite material may include one or more of polycarbonate/glass fiber, polycarbonate/acrylic alloy, polycarbonate/ABS alloy, polysulfone/polycarbonate alloy, or polycarbonate/copolyester, liquid crystal polymer or glass reinforced liquid crystal polymer.

Also, the polymeric shell may include a plurality of cavities for receiving the one or more teeth, where the first predetermined position and the second predetermined position may correspond at least in part to an orthodontic treatment for the one or more teeth.

A method of orthodontic treatment in accordance with still yet another embodiment may include positioning a first appliance substantially around one or more teeth during a first portion of a recurring time period to apply a first predetermined force or predetermined tooth movement on the one or more teeth, the first appliance formed of a first material, positioning a second appliance substantially around the one or more teeth during a second portion of the recurring time period to apply a second predetermined force or predetermined tooth movement on the one or more teeth, the second appliance formed of a second material, where at least one of the first portion and the second portion of the recurring time period is repeated at least once such that at least one of the first appliance or the second appliance is positioned again substantially around the one or more teeth during the respective first or second portion of the recurring time period.

The recurring time period may be repeated, and further, where the first portion and the second portion of each repeated recurring time period are nonoverlapping.

The first material may include an amorphous thermoplastic which may include one or more of polycarbonate, thermoplastic urethane, acrylic, polysulfone, polyprolylene, polypropylene/ethylene copolymer, or polyester/polycarbonate copolymer.

The second material may include a semi-crystalline thermoplastic, such as, for example, polyamide, polyethylene terephthalate. polybutylene terephthalate, polyetherimide, polyetheretherketone, polyethersulfone, or polytrimethylene terephthalate.

The second material may further include one or more filler material such as one or more of carbon, mineral, silica or titanium.

In another aspect, the second material may include a copolymer or a composite material such as one or more of carbon/polycarbonate/glass fiber, polycarbonate/acrylic alloy, polycarbonate/ABS alloy, polysulfone/polycarbonate alloy, or polycarbonate/copolyester, liquid crystal polymer or glass reinforced liquid crystal polymer.

The first predetermined force or predetermined tooth movement may be less than the second predetermined force or predetermined tooth movement, or alternatively, the first predetermined force or predetermined tooth movement may be substantially equal to the second predetermined force or predetermined tooth movement.

Additionally, the one or more of the first appliance and the second appliance may have a relatively higher opacity than the other one of the first appliance and the second appliance.

Moreover, the one of the first appliance and the second appliance may be configured primarily to retain the position of the one or more teeth, and further, where the other one of the first appliance and the second appliance may be configured to primarily displace the position of the one or more teeth.

The one of the first appliance and the second appliance in another aspect may be substantially translucent while the other one of the first appliance and the second appliance may be substantially opaque.

In another aspect, each of the first appliance and the second appliance may include one or more cavities formed substantially to surround a respective one or more of the teeth, and further, where the cavity geometry of the first appliance and the second appliance may be substantially the same.

Also, each of the first appliance and second appliance may include a plurality of dental aligners, a first of the plurality of dental aligners including an upper teeth dental aligner and a lower teeth dental aligner, where one or more of the upper teeth dental aligner or the lower teeth aligner may be formed of one of a clear material or a colored material.

In a further aspect, the first portion and the second portion of the recurring time period may include one or more of a sleeping time period and a nonsleeping time period, respectively, a weekday time period and a weekend time period, respectively, an outdoor time period and an indoor time period, respectively, or a social time period and a non social time period, respectively.

Additionally, the first portion and the second portion of the recurring time period each may correspond to one of a relatively faster movement of the one or more teeth or a relatively slower movement of the one or more teeth.

Furthermore, after a predetermined number of recurring time periods the first appliance and the second appliance may be modified to apply a modified first predetermined force or predetermined tooth movement and a modified second predetermined force or predetermined tooth movement on the one or more teeth, and also, where the first appliance and the second appliance each may include one or more cavities for substantially surrounding the one or more teeth such that, the one or more cavities are modified after the predetermined number of recurring time periods.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of orthodontic treatment, comprising:
    positioning a first appliance substantially around one or more teeth during a first portion of a recurring time period to apply one of a first predetermined force or a predetermined tooth movement on the one or more teeth, the first appliance formed of a first material and intended for a treatment stage of a treatment plan comprising a plurality of treatment stages; and
    positioning a second appliance substantially around the one or more teeth during a second portion of the recurring time period to apply one of a second predetermined force or a predetermined tooth movement on the one or more teeth, the second appliance formed of a second material and intended for the same treatment stage as the first appliance, wherein the first and second materials are different and cavity geometries of the first appliance and the second appliance are substantially the same;
        wherein the first portion and the second portion of the recurring time period are each repeated at least once such that both the first appliance and the second appliance are alternatingly positioned again substantially around the one or more teeth during the respective first or second portion of the recurring time period after the other of the first appliance or the second appliance is removed until the treatment stage is completed.

2. The method of claim 1 wherein the recurring time period is repeated, and further, wherein the first portion and the second portion of each repeated recurring time period are nonoverlapping.

3. The method of claim 1 wherein the first material includes an amorphous thermoplastic.

4. The method of claim 3 wherein the amorphous thermoplastic includes one or more of polycarbonate, thermoplastic urethane, acrylic, polysulfone, polyprolylene, polypropylene/ethylene copolymer, or polyester/polycarbonate copolymer.

5. The method of claim 3 where the second material includes a semi-crystalline thermoplastic.

6. The method of claim 5 wherein the semi-crystalline thermoplastic includes polyamide, polyethylene terephthalate. polybutylene terephthalate, polyetherimide, polyetheretherketone, polyethersulfone, or polytrimethylene terephthalate.

7. The method of claim 3 wherein the second material includes a copolymer or a composite material.

8. The method of claim 7 wherein the copolymer or the composite material includes one or more of polycarbonate and glass fiber, polycarbonate and acrylic alloy, polycarbonate and ABS alloy, polysulfone and polycarbonate alloy, polycarbonate and copolyester, liquid crystal polymer or glass reinforced liquid crystal polymer.

9. The method of claim 1, wherein the second material further includes one or more filler material.

10. The method of claim 9 wherein the one or more filler material includes one or more of carbon, mineral, silica or titanium.

11. The method of claim 1 wherein one of the first predetermined force or the predetermined tooth movement is less than the respective one of the second predetermined force or the predetermined tooth movement.

12. The method of claim 1 wherein the one of the first predetermined force or the predetermined tooth movement is substantially equal to the respective one of the second predetermined force or the predetermined tooth movement.

13. The method of claim 1 wherein one of the first appliance and the second appliance has a relatively higher opacity than the other one of the first appliance and the second appliance.

14. The method of claim 1 wherein one of the first appliance and the second appliance is configured primarily to retain the position of the one or more teeth, and further, wherein the other one of the first appliance and the second appliance is configured to primarily displace the position of the one or more teeth.

15. The method of claim 1 wherein one of the first appliance and the second appliance is substantially translucent, and further, wherein the other one of the first appliance and the second appliance is substantially opaque.

16. The method of claim 1 wherein each of the first appliance and second appliance includes a plurality of dental aligners, wherein one of the plurality of dental aligners includes an upper teeth dental aligner and a lower teeth dental aligner.

17. The method of claim 16 wherein one or more of the upper teeth dental aligner or the lower teeth aligner is formed of one of a clear material or a colored material.

18. The method of claim 1 wherein the first portion and the second portion of the recurring time period includes one or more of a sleeping time period and a nonsleeping time period, respectively, a weekday time period and a weekend time period, respectively, an outdoor time period and an indoor time period, respectively, a jaw functioning and a non-functioning time, or a social time period and a non social time period, respectively.

19. The method of claim 1 wherein the first portion and second portion of the recurring time period each corresponds to one of a relatively faster movement of the one or more teeth or a relatively slower movement of the one or more teeth.

20. The method of claim 1 wherein after a predetermined number of recurring time periods the first appliance and the second appliance are modified to apply one of a modified first predetermined force or a predetermined tooth movement and one of a modified second predetermined force or a predetermined tooth movement on the one or more teeth.

21. The method of claim 20 wherein the first appliance and the second appliance each include one or more cavities for substantially surrounding the one or more teeth such that, the one or more cavities are modified after the predetermined number of recurring time periods.

22. A method of orthodontic treatment, comprising:
positioning a first appliance substantially around one or more teeth during a first portion of a recurring time period to apply one of a first predetermined force or a predetermined tooth movement on the one or more teeth, the first appliance formed of a first material; and
positioning a second appliance substantially around the one or more teeth during a second portion of the recurring time period to apply one of a second predetermined force or a predetermined tooth movement on the one or more teeth, the second appliance formed of a second material, wherein cavity geometries of the first appliance and the second appliance are substantially the same;
wherein the first appliance and second appliance are alternatingly positioned more than once substantially around the one or more teeth during the recurring time period after the other of the first appliance or the second appliance is removed and wherein the first appliance has a stiffness different from that of the second appliance.

23. The method of claim 22, wherein the first material has clarity of approximately 80 percent or more.

24. The method of claim 23, wherein the first material includes one or more of amorphous thermoplastic polymer, semi-crystalline thermoplastic polymer, transparent thermoplastic polymer with one or more filler or nanofiller material, polycarbonate, thermoplastic polyurethane, acrylic, polysulfone, polypropylene, polypropylene and ethylene copolymer, polyester and polycarbonate copolymer, styrenic polymeric material, polyamide, polymethylpentene and polyetheretherketone.

25. The method of claim 23, wherein the second material has clarity of less than approximately 80 percent.

26. The method of claim 25, wherein the second material includes semi-crystal thermoplastic, crystalline thermoplastic, polyamide, polyethylene terephthalate. polybutylene terephthalate, polyetherimide, polyetheretherketone, polyethersulfone, or polytrimethylene terephthalate, or one or more composites with one or more filler or nanofiller.

27. The method of claim 23, wherein the second material includes a copolymer, a blend of polymers, or a composite material.

28. The method of claim 27, wherein the copolymer or the composite material includes one or more of polycarbonate and glass fiber, polycarbonate and acrylic alloy, polycarbonate and ABS alloy, polysulfone and polycarbonate alloy, polycarbonate and copolyester, liquid crystal polymer or glass reinforced liquid crystal polymer.

29. The method of claim 22, wherein one or more of the first material and the second material further includes one or more filler material or nanofiller material.

30. The method of claim 29, wherein the one or more filler material or the nanofiller material includes one or more of carbon, mineral, silica or titanium, metal oxide, oxygenate, halide, sulfate, short or long glass fiber, synthetic alumina nanofiller, aluminorganic nanofiller, calcium carbonate nanofiller, ceramic nanofiller, carbon black nanofiller, carbon nanotube nanofiller, carbon fiber nanofiller, cellulose nanofiller, activated clay nanofiller, natural clay nanofiller, synthetic clay nanofiller, organo clay nanofiller, natural fiber nanofiller, graphite nanofiller, magnesium hydroxide nanofiller, mineral nanofiller, montmorillonite clay nanofiller, phosphate nanofiller, poly oligomeric silsesquioxane (POSS) nanofiller, silica nanofiller, silver nanofiller, talc nanofiller, organo-titanate nanofiller, titanium white nanofiller, or zinc oxide nanofiller.

31. The method of claim 22, wherein one of the first predetermined force or the predetermined tooth movement is less than a respective one of the second predetermined force or the predetermined tooth movement.

32. The method of claim 22, wherein one of the first appliance and the second appliance has a relatively higher opacity than the other one of the first appliance and the second appliance.

33. The method of claim 22, wherein one of the first appliance and the second appliance is configured primarily to retain the position of the one or more teeth, and wherein the other one of the first appliance and the second appliance is configured to primarily displace the position of the one or more teeth.

34. The method of claim 22, wherein one of the first appliance and the second appliance is substantially translucent, and wherein the other one of the first appliance and the second appliance is substantially opaque.

35. The method of claim 22, wherein each of the first appliance and second appliance includes a plurality of dental aligners, wherein one of the plurality of dental aligners includes an upper teeth dental aligner and a lower teeth dental aligner.

36. The method of claim 35, wherein one or more of the upper teeth dental aligner or the lower teeth aligner is formed of one of a clear material or a colored material.

37. The method of claim 22, wherein the first portion and the second portion of the recurring time period includes one or more of a sleeping time period and a nonsleeping time period, respectively, a weekday time period and a weekend time period, respectively, an outdoor time period and an indoor time period, respectively, or a social time period and a non social time period, respectively.

38. The method of claim 22, wherein the first portion and the second portion of the recurring time period each corresponds to one of a relatively faster movement of the one or more teeth or a relatively slower movement of the one or more teeth.

39. The method of claim 22, wherein after a predetermined number of recurring time periods the first appliance and the second appliance are modified to apply one of a modified first predetermined force or a predetermined tooth movement and one of a modified second predetermined force or a predetermined tooth movement on the one or more teeth.

40. The method of claim 39, wherein the first appliance and the second appliance each includes one or more cavities for substantially surrounding the one or more teeth such that the one or more cavities are modified after the predetermined number of recurring time periods.

* * * * *